(12) United States Patent
Konishi et al.

(10) Patent No.: US 10,690,688 B2
(45) Date of Patent: Jun. 23, 2020

(54) AUTOMATIC ANALYZER

(71) Applicant: Hitachi High-Technologies Corporation, Minato-ku, Tokyo (JP)

(72) Inventors: Rei Konishi, Tokyo (JP); Akihisa Makino, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

(21) Appl. No.: 16/325,885

(22) PCT Filed: Aug. 4, 2017

(86) PCT No.: PCT/JP2017/028355
§ 371 (c)(1),
(2) Date: Feb. 15, 2019

(87) PCT Pub. No.: WO2018/047545
PCT Pub. Date: Mar. 15, 2018

(65) Prior Publication Data
US 2019/0212351 A1 Jul. 11, 2019

(30) Foreign Application Priority Data
Sep. 8, 2016 (JP) .................. 2016-175179

(51) Int. Cl.
*G01N 35/00* (2006.01)
*G01N 35/10* (2006.01)
(Continued)

(52) U.S. Cl.
CPC ....... *G01N 35/00584* (2013.01); *G01N 35/02* (2013.01); *G01N 35/1002* (2013.01);
(Continued)

(58) Field of Classification Search
None
See application file for complete search history.

(56) References Cited

U.S. PATENT DOCUMENTS

2015/0316532 A1  11/2015  Makino et al.

FOREIGN PATENT DOCUMENTS

EP  2 317 326 A1  5/2011
EP  2 365 342 A2  9/2011
(Continued)

OTHER PUBLICATIONS

International Search Report (PCT/ISA/210) issued in PCT Application No. PCT/JP2017/028355 dated Oct. 17, 2017 with English translation (six (6) pages).
(Continued)

*Primary Examiner* — Kathryn Wright
(74) *Attorney, Agent, or Firm* — Crowell & Moring LLP

(57) ABSTRACT

Provided are an automatic analyzer and an analysis method for the automatic analyzer, the analyzer including a dispensing mechanism having a nozzle part for dispensing a liquid; a liquid supply part for supplying the liquid to the dispensing mechanism; a temperature increasing part for increasing the temperature of liquid to be supplied from the liquid supply part to the dispensing mechanism; and a control part for controlling the dispensing mechanism, the temperature increasing part, and the liquid supply part. In accordance with information relating to whether a requested analysis is continually performed, the control unit controls the liquid supply part such that, if the analysis is not continually performed, the temperature of liquid supplied from the liquid supply part is increased by the temperature increasing part, and the liquid of the increased temperature is then supplied to the nozzle part of the dispensing mechanism.

9 Claims, 7 Drawing Sheets

(51) Int. Cl.
*G01N 35/02* (2006.01)
*G01N 33/86* (2006.01)

(52) U.S. Cl.
CPC ......... *G01N 35/1004* (2013.01); *G01N 33/86* (2013.01); *G01N 2035/00425* (2013.01)

(56) References Cited

FOREIGN PATENT DOCUMENTS

| | | |
|---|---|---|
| EP | 2 860 528 A1 | 4/2015 |
| JP | 6-40837 U | 5/1994 |
| JP | 9-34731 A | 2/1997 |
| JP | 2008-256492 A | 10/2008 |
| WO | WO 2014/103744 A1 | 7/2014 |

OTHER PUBLICATIONS

Japanese-language Written Opinion (PCT/ISA/237) issued in PCT/JP2017/028355 dated Oct. 17, 2017 (four (4) pages).
Extended European Search Report issued in European Application No. 17848489.5 dated Mar. 20, 2020 (eight (8) pages).

[FIG. 1]
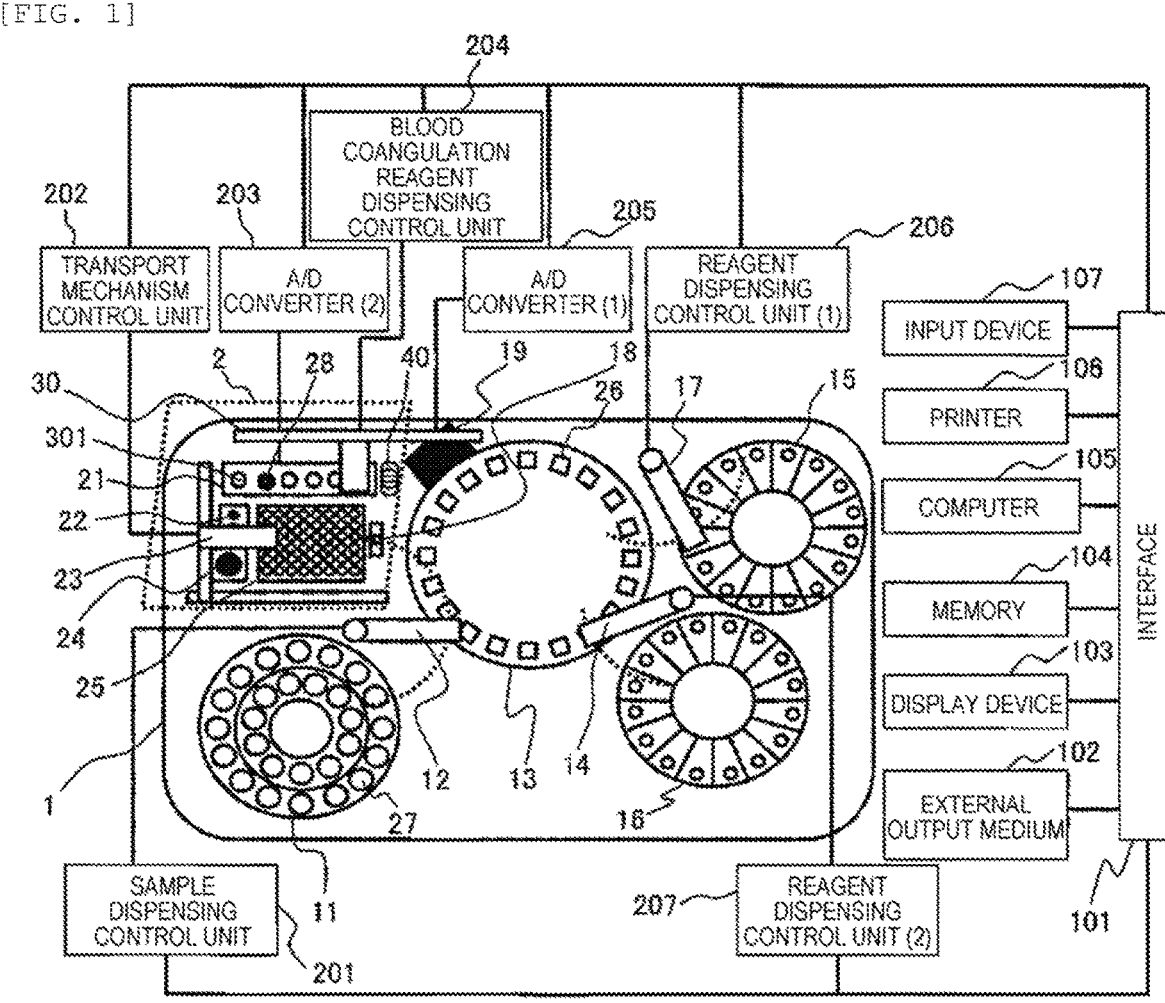

[FIG. 2]
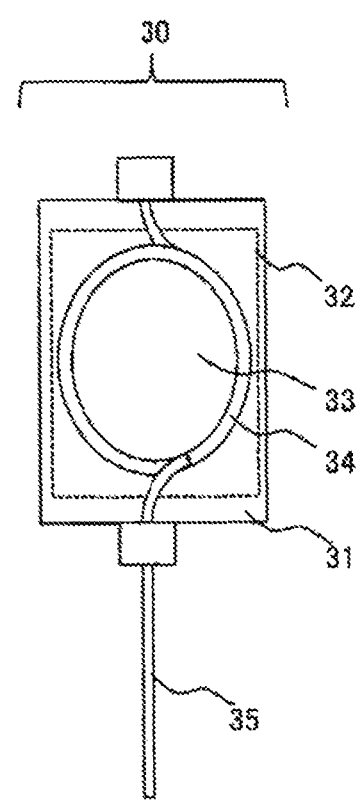

[FIG. 3]
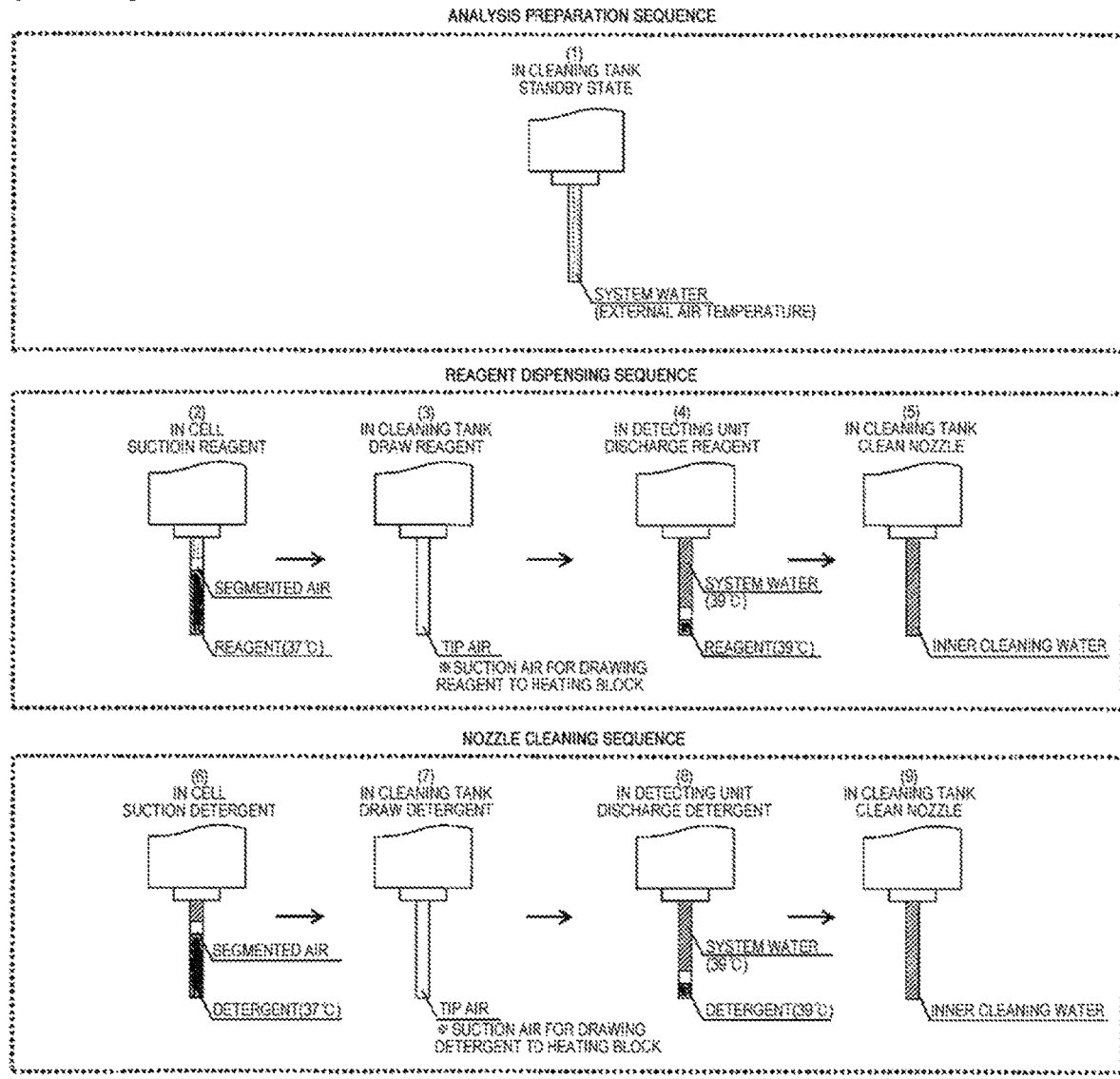

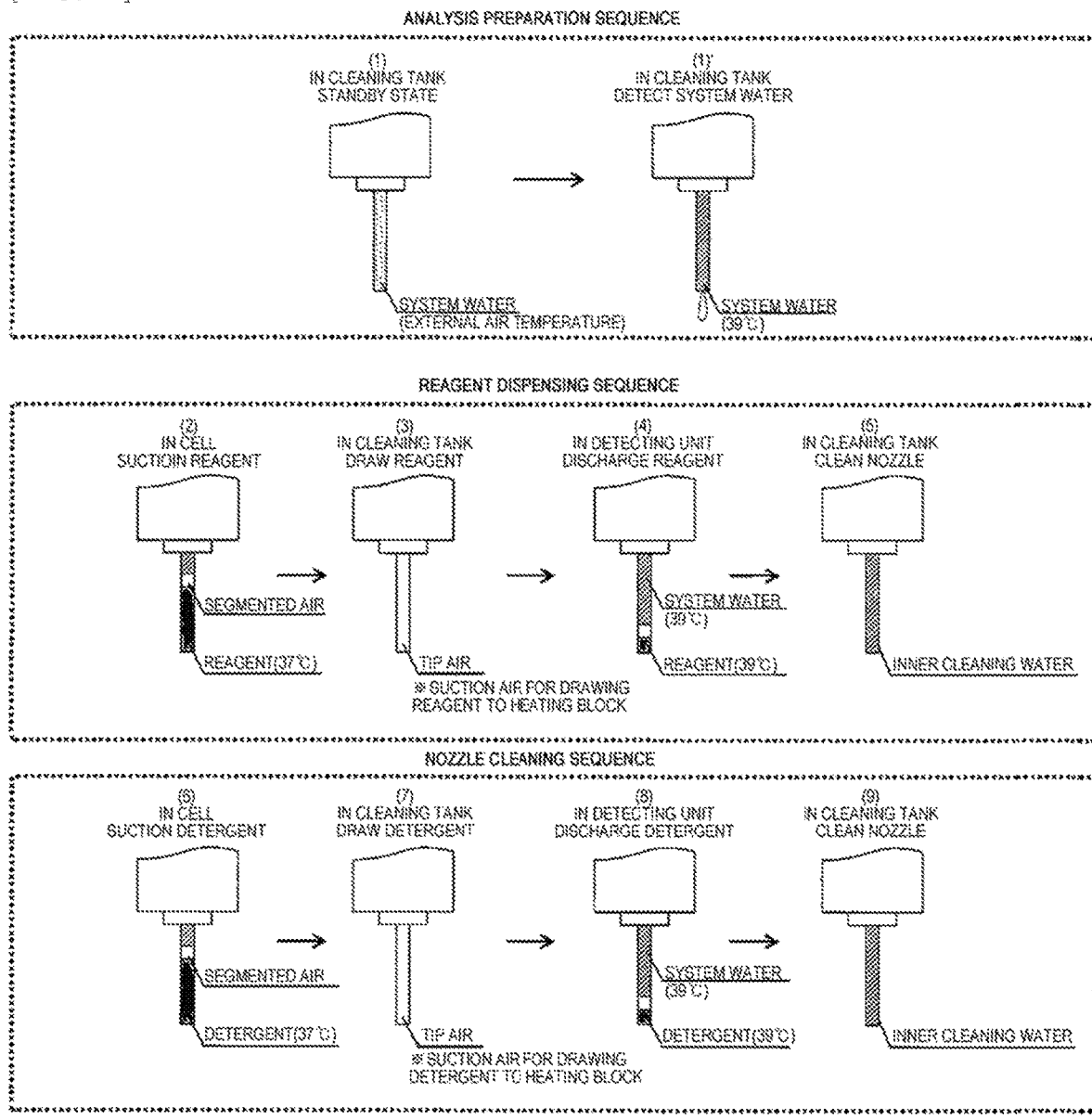

[FIG. 5]
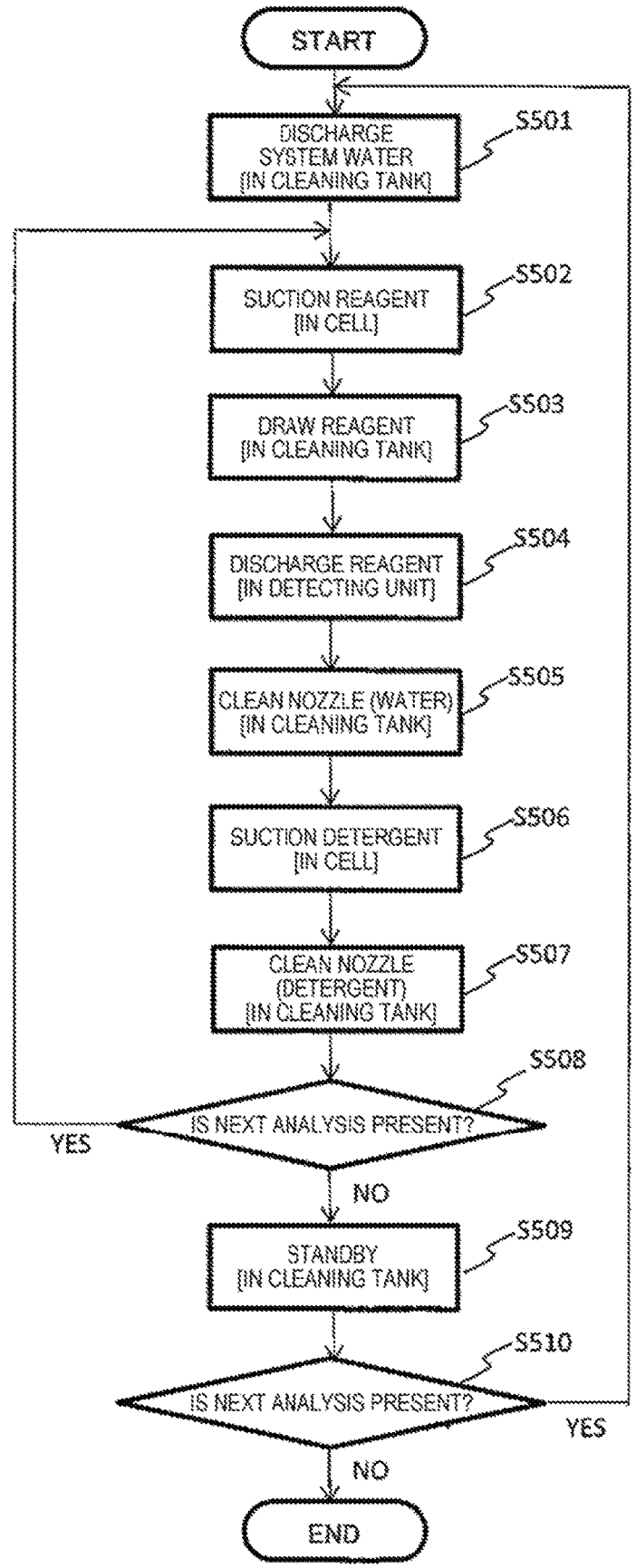

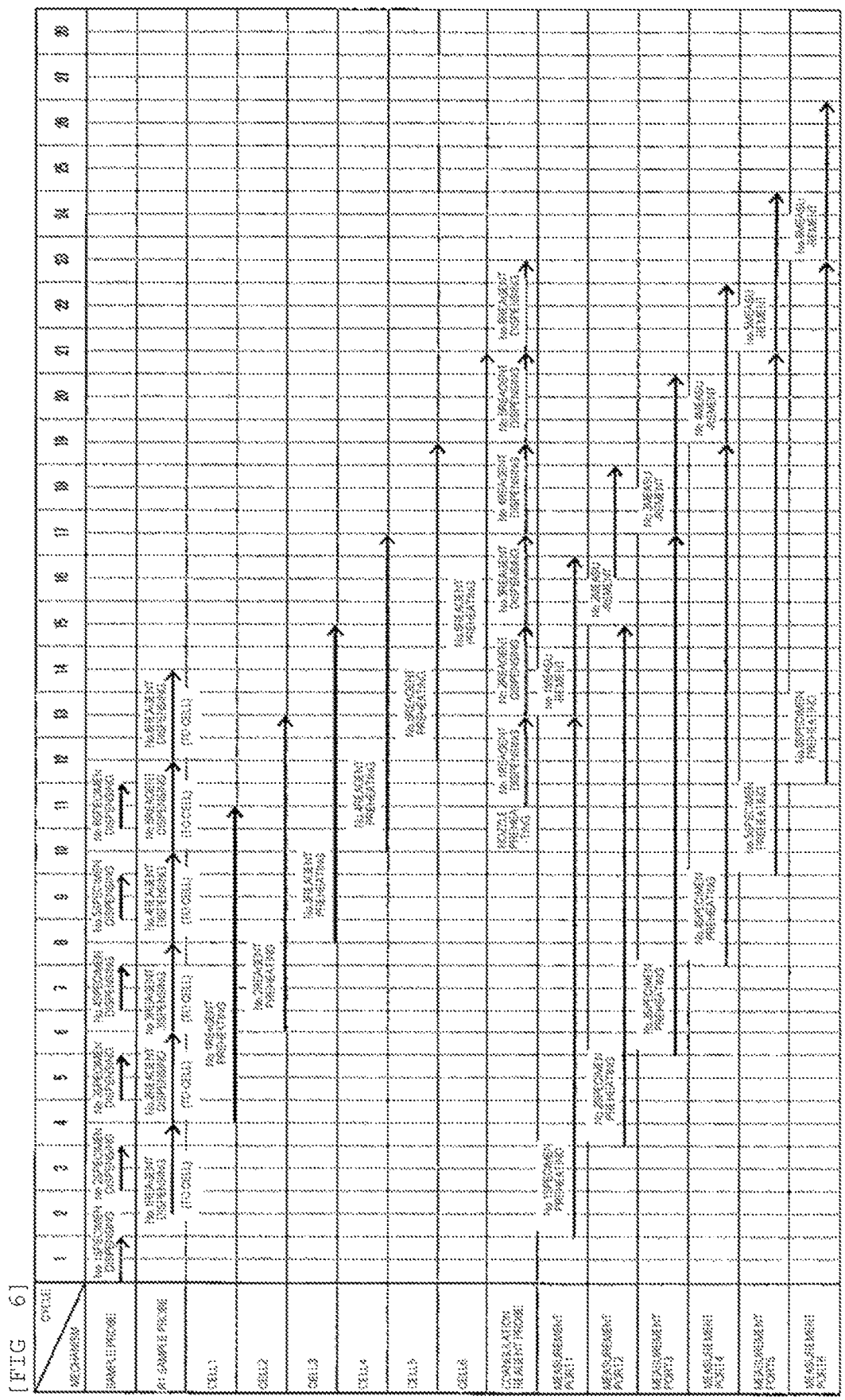
[FIG. 6]

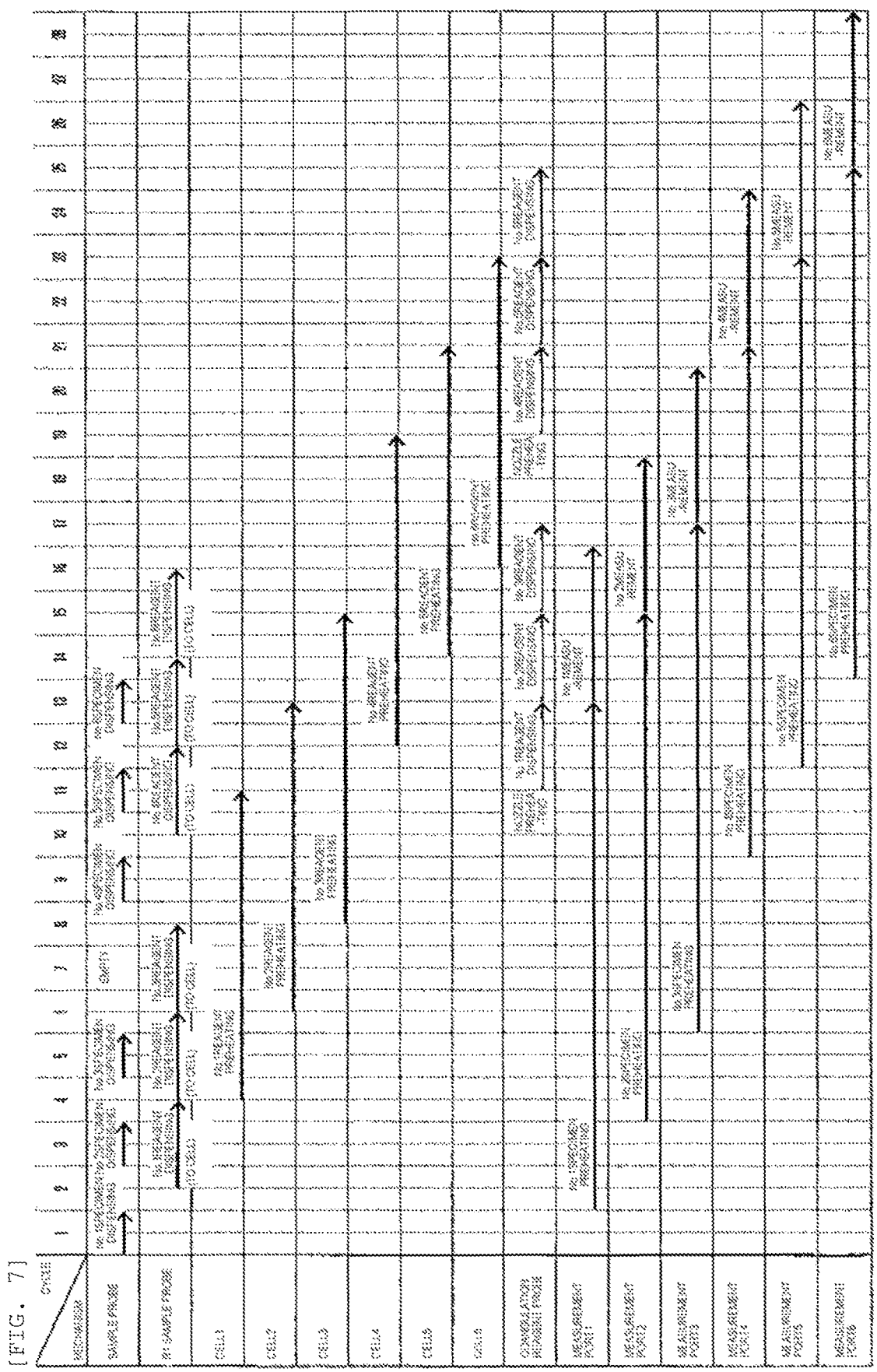

AUTOMATIC ANALYZER

TECHNICAL FIELD

The present invention relates to an automatic analyzer that automatically analyzes a component included in a biological sample such as blood and particularly relates to an automatic analyzer in which a temperature adjusting mechanism is provided in a dispensing mechanism.

BACKGROUND ART

Examples of the automatic analyzer include a device for biochemical analysis that performs qualitative and quantitative analysis of a target component in a biological sample in the field of a biological examination or a hematological examination or the like and a device for blood coagulation analysis that measures coagulability of blood as a sample.

For an item of the latter blood coagulation analysis, the reaction time is shorter than that of the former analysis, and it is necessary to start the measurement from the time when a specimen and a reagent are stirred. Therefore, when the two liquids are mixed with each other, it is necessary to control the temperature of the liquid mixture to 37° C. As a method of controlling the temperature of the liquid mixture, a method of increasing the temperature of a liquid before discharging the liquid is known.

Regarding the technique of increasing the temperature of a liquid before discharging the liquid, JP-A-2008-256492 (PTL 1) describes a device that cleans a DNA chip, the device including: a liquid delivery pump that delivers a cleaning solution; an injection nozzle that injects the delivered cleaning solution to a chip; a liquid delivery tube that connects the liquid delivery pump and the injection nozzle to each other; and a heating block that is provided halfway the liquid delivery tube and heats the liquid in the liquid delivery tube, wherein the cleaning solution in the liquid delivery tube between the injection nozzle and the heating block is delivered to the heating block to be warmed up before an initial cleaning operation, and the warmed cleaning solution is delivered to the injection nozzle such that the cleaning solution at an appropriate temperature is discharged from the initial cleaning operation.

CITATION LIST

Patent Literature

PTL 1: JP-A-2008-256492

SUMMARY OF INVENTION

Technical Problem

As described above, in the blood coagulation analysis in which it is necessary to start the measurement from the time when a specimen and a reagent are stirred, when the two liquids are mixed with each other, it is necessary to control the temperature of the liquid mixture to 37° C.

Here, there is a difference between the temperature of a reagent to be discharged for the first specimen and the temperature of a reagent to be discharged for the second specimen onwards, the first specimen being the first analysis target after the automatic analyzer is switched from a standby state to an analysis state, and the second specimen onwards being the analysis target after the first specimen. That is, in the first specimen analysis, a nozzle of a dispensing mechanism has been cooled by external air while the device is in the standby state, and thus is in a cooled state. Therefore, while the reagent passes through the nozzle, the nozzle steals heat from the heated reagent such that the temperature of the reagent decreases. On the other hand, in the second specimen analysis onwards, the reagent heated during preceding analysis operations is suctioned and discharged. Therefore, the temperature of the nozzle itself has been warmed up, and the amount of heat which the nozzle steals from the liquid is less than that of the first specimen analysis. In the blood coagulation analysis, this temperature difference of the reagent may affect analysis results. Therefore, in order to realize high-accuracy analysis, it is particularly required to perform a stable temperature adjustment irrespective of the analysis order.

In the configuration described in PTL 1, by heating the heating block before discharging the cleaning solution using the above-described method, the cleaning solution delivered to the injection nozzle during discharging is adjusted to temperature conditions suitable for cleaning the DNA chip. However, in this method, since the cleaning solution is a target to be heated, the above-described problem, which is the difference between the temperature of the reagent discharged for the first specimen after the device starts analysis from the standby state and the temperature of the reagent discharged for the second specimen onwards, is not considered.

The present invention has been made in consideration of the above-described problem and relates to a technique in which, when a reagent passing through a nozzle, the temperature of the reagent is maintained to be constant irrespective of the analysis order such that the temperature of a liquid mixture of a specimen and the reagent at the start of measurement is stabilized and high-accuracy analysis is realized.

Solution to Problem

According to one aspect for solving the above-described problem, there are provided an automatic analyzer and an analysis method for the automatic analyzer, the analyzer comprising: a dispensing mechanism having a nozzle part for dispensing a liquid; a liquid supply part for supplying the liquid to the dispensing mechanism; a temperature increasing part for increasing the temperature of liquid to be supplied from the liquid supply part to the dispensing mechanism; and a control part for controlling the dispensing mechanism, the temperature increasing part, and the liquid supply part. In accordance with information relating to whether a requested analysis is continually performed, the control unit controls the liquid supply part such that, if the analysis is not continually performed, the temperature of liquid supplied from the liquid supply part is increased by the temperature increasing part, and the liquid of the increased temperature is then supplied to the nozzle part of the dispensing mechanism.

Advantageous Effects of Invention

According to the above-described aspect, by performing a control in consideration of a decrease in the temperature of the nozzle affected by the analysis order, when a liquid passes through the nozzle, the temperature of the liquid can be maintained to be constant even at any analysis timing. As a result, the temperature of the liquid mixture of the sample and the reagent can be controlled with high accuracy, and high-reliability analysis can be realized.

BRIEF DESCRIPTION OF DRAWINGS

FIG. 1 is a diagram illustrating a basic configuration of an automatic analyzer according to an embodiment.

FIG. 2 is a diagram illustrating a configuration of a blood coagulation reagent dispensing mechanism according to the embodiment (first embodiment).

FIG. 3 is a diagram illustrating a series of operations of the blood coagulation reagent dispensing mechanism to which an operation of supplying heated system water is not applied.

FIG. 4 is a diagram illustrating a series of operations of the blood coagulation reagent dispensing mechanism to which the operation of supplying heated system water according to the embodiment (first embodiment) is applied.

FIG. 5 is a flowchart illustrating the series of operations of the blood coagulation reagent dispensing mechanism to which the operation of supplying heated system water according to the embodiment (first embodiment) is applied.

FIG. 6 is a time chart illustrating a series of operations of blood coagulation analysis (during continuous analysis) according to the embodiment (first embodiment).

FIG. 7 is a time chart illustrating a series of operations of blood coagulation analysis (during intermittent analysis) according to the embodiment (first embodiment).

DESCRIPTION OF EMBODIMENTS

Hereinafter, an embodiment of the present invention will be described with reference to the drawings. In all the drawings, components having the same functions are represented by the same reference numerals in principle, and description thereof will not be repeated.

First Embodiment

<Overall Configuration of Device>

FIG. 1 is a diagram illustrating a basic configuration of an automatic analyzer according to the embodiment. Here, as an aspect of the automatic analyzer, a composite type automatic analyzer including a turntable type biochemical analyzing part and a blood coagulation time analyzing unit will be described.

As illustrated in the drawing, in the automatic analyzer 1, mainly, a reaction disk 13, a sample disk 11, a first reagent disk 15, a second reagent disk 16, a blood coagulation time analyzing unit 2, a photometer 19 are arranged on a housing.

The reaction disk 13 is a disk-shaped unit that is rotatable clockwise and counterclockwise, in which plural reaction containers 26 can be arranged on a circumference thereof.

The sample disk 11 is a disk-shaped unit that is rotatable clockwise and counterclockwise, in which plural sample container 27 each of which stores a sample such as a standard sample or a test sample can be arranged on a circumference thereof.

The first reagent disk 15 and the second reagent disk 16 are disk-shaped units that are rotatable clockwise and counterclockwise, in which plural reagent containers each of which stores a reagent including a component that is reactive with a component of each examination item included in the sample can be arranged on a circumference thereof. In addition, although not illustrated in the drawing, the first reagent disk 15 and the second reagent disk 16 may include a cooling mechanism or the like such that the reagent in the arranged reagent container can be cooled.

A sample dispensing mechanism 12 is arranged between the sample disk 11 and the reaction disk 13. Due to a rotation operation of the sample dispensing mechanism 12, a dispensing operation such as suction or discharge of the sample can be performed on the sample container 27 on the sample disk 11, the reaction container (for biochemical analysis) 26 on the reaction disk 13, and a reaction container (for blood coagulation analysis) 28 at a sample dispensing position 18 of the blood coagulation time analyzing unit 2.

Likewise, a first reagent dispensing mechanism 17 is arranged between the first reagent disk 15 and the reaction disk 13, and a second reagent dispensing mechanism 14 is arranged between the second reagent disk 16 and the reaction disk 13. Due to respective rotation operations of the first reagent dispensing mechanism 17 and the second reagent dispensing mechanism 14, a dispensing operation such as suction or discharge can be performed on the reaction container 26 on the reaction disk 13 and the reagent containers on the first reagent disk 15 and the second reagent disk 16.

The blood coagulation time analyzing unit 2 mainly includes a blood coagulation time detecting part 21, a blood coagulation reagent dispensing mechanism 30, a disposable reaction container magazine 25, the sample dispensing position 18, a reaction container transport mechanism 23, a reaction container disposal hole 24, an optical jig magazine 22, and a cleaning tank 40 for a blood coagulation reagent dispensing mechanism. Here, the blood coagulation time detecting part 21 includes plural reaction ports 301 including: a reaction container holding part (not illustrated) that can hold the reaction container (for blood coagulation analysis) 28; a light source that emits light to the held reaction container (for blood coagulation analysis) 28; and a detector that detects the emitted light. In addition to the cleaning tank 40 for a blood coagulation reagent dispensing mechanism, as cleaning tanks (not illustrated), cleaning tanks are arranged for the sample dispensing mechanism 12, the first reagent dispensing mechanism 17, and the second reagent dispensing mechanism 14, respectively. Here, outer cleaning water for cleaning a nozzle outer wall of each of the dispensing mechanisms is discharged from each of the cleaning tanks. System water is supplied from a water supply tank to each of the dispensing mechanisms by a liquid delivery pump (not illustrated) (the water supply tank and the liquid delivery pump will also be collectively referred to as "liquid supply part").

Here, a detailed configuration of the blood coagulation reagent dispensing mechanism 30 according to the embodiment will be described using FIG. 2. As illustrated in FIG. 2, in the blood coagulation reagent dispensing mechanism 30, a heating block 31, a heating part 32, a temperature measuring part 33, a nozzle part 35, and a heating pipe 34 are arranged. In the temperature measuring part 33, a temperature sensor is arranged. As the temperature sensor, for example, a thermistor or a thermocouple can be used. In the heating part 32, a heater is arranged in the heating block 31. Thermal energy input to the heater is transmitted to the heating pipe 34 through the heating block 31 such that the thermal energy is applied to a liquid in the heating pipe 34. The heating pipe 34 is embedded in the heating block 31. In the blood coagulation reagent dispensing mechanism 30, the liquid is suctioned, and then air is suctioned. As a result, the liquid is drawn to the heating part 32 of the heating block 31 such that the liquid can be heated. The heating block 31, the heating pipe 34, and the nozzle part 35 are formed of a metal material that is not likely to be corroded and has a high thermal conductivity, for example, aluminum or stainless steel.

Returning to FIG. 1, a control system and a signal processing system relating to the automatic analyzer 1 will be simply described. A computer 105 is connected to a sample dispensing control unit 201, a reagent dispensing control unit (1) 206, a reagent dispensing control unit (2) 207, a blood coagulation reagent dispensing control unit 204, an A/D converter (1) 205, an A/D converter (2) 203, and a transport mechanism control unit 202 through an interface 101 and transmits a signal as an instruction to each of the control units.

The sample dispensing control unit 201 controls the sample dispensing operation of the sample dispensing mechanism 12 on the basis of an instruction received from the computer 105.

In addition, the reagent dispensing control unit (1) 206 and the reagent dispensing control unit (2) 207 control the reagent dispensing operation of the first reagent dispensing mechanism 17 and the second reagent dispensing mechanism 14 on the basis of an instruction received from the computer 105.

In addition, the transport mechanism control unit 202 controls the operation of the reaction container transport mechanism 23 transporting the disposable reaction container (for blood coagulation analysis) 28 between the reaction container magazine 25, the sample dispensing position 18, the reaction port 301 of the blood coagulation time detecting part 21, and the reaction container disposal hole 24 on the basis of an instruction received from the computer 105.

The blood coagulation reagent dispensing control unit 204 converts an electric signal output from temperature measuring part 33 into a measured temperature, calculates a difference between the measured temperature and a target temperature, and controls an output of the heating part 32 such that the temperature of the heating block 31 can be controlled to be constant. When two liquids of a specimen and a reagent are mixed with each other, in order to control the temperature of the liquid mixture to 37° C., the target temperature of the heating block 31 may be set to be higher than 37° C. In addition, by changing the set temperature depending on the external air temperature, the temperature can be accurately controlled. For example, when the external air temperature is represented by x° C. and the target temperature is represented by y° C., it is preferable to set the target temperature as $y=-0.1x+40$. In addition, the blood coagulation reagent dispensing control unit 204 causes the blood coagulation reagent dispensing mechanism 30 to dispense a reagent for blood coagulation into the reaction container (for blood coagulation analysis) 28 storing the sample that is dispensed by the sample dispensing mechanism 12 transported to the reaction port 301 on the basis of an instruction received from the computer 105. Alternatively, the blood coagulation reagent dispensing control unit 204 causes the blood coagulation reagent dispensing mechanism 30 to dispense a pre-treatment solution into the empty reaction container (for blood coagulation analysis) 28, the pre-treatment solution being a liquid mixture that is obtained by mixing the sample and a first reagent for blood coagulation analysis with each other in the reaction container (for biochemical analysis) 26. In this case, subsequently, the blood coagulation reagent dispensing control unit 204 causes the blood coagulation reagent dispensing mechanism 30 to dispense a second reagent for blood coagulation analysis into the reaction container (for blood coagulation analysis) 28 storing the pre-treatment solution. Here, the reagents for blood coagulation analysis are arranged in the first reagent disk 15 and the second reagent disk 16 and are used for blood coagulation analysis after being temporarily dispensed into the reaction container (for biochemical analysis) 26 on the reaction disk 13 by the first reagent dispensing mechanism 17 and the second reagent dispensing mechanism 14 as necessary.

A photometric value of transmitted light or scattered light in the reaction solution of the reaction container (for biochemical analysis) 26 that is converted into a digital signal by the A/D converter (1) 205 and a photometric value of transmitted light or scattered light in the reaction solution of the disposable reaction container (for blood coagulation analysis) 28 that is converted into a digital signal by the A/D converter (2) 203 are input to the computer 105.

A printer 106 for printing a measurement result as a report or the like, a memory 104 as a storage device, an external output medium 102, an input device 107 such as a keyboard for inputting an operation instruction or the like, and a display device 103 for displaying a screen are connected to the interface 101. Examples of the display device 103 include a liquid crystal display and a CRT display.

Analysis of a biochemical analytical item by the automatic analyzer 1 is performed according to the following procedure. First, an operator requests an examination item for each sample using the input device 107 such as a keyboard. In order to analyze the sample for the requested examination item, the sample dispensing mechanism 12 dispenses a predetermined amount of the sample from the sample container into the reaction container (for biochemical analysis) 26 according to analysis parameters.

The reaction container (for biochemical analysis) 26 into which the sample is dispensed is transported by the rotation of the reaction disk 13 and stops at a reagent receiving position. A pipette nozzles of each of the first reagent dispensing mechanism 17 and the second reagent dispensing mechanism 14 dispense a predetermined amount of reagent solution into the reaction container (for biochemical analysis) 26 according to analysis parameters of the corresponding examination item. Regarding the dispensing order of the sample and the reagent, the reagent may be dispensed before the sample contrary to the example.

Next, the sample and the reagent are stirred and mixed using a stirring mechanism (not illustrated). When the reaction container (for biochemical analysis) 26 crosses a photometric position, photometry of transmitted light or scattered light of the reaction solution is performed using the photometer. The transmitted light or the scattered light having undergone photometry is converted into numeric data in proportion to the light amount by the A/D converter (1) 205, and the numeric data is input to the computer 105 through the interface 101.

Concentration data is calculated on the basis of a calibration curve measured in advance using the converted numerical value with an analysis method designated per examination item. The component concentration data as the analysis result of each examination item is output to the printer 106 or the screen of the display device 103.

Before performing the above-described measuring operation, the operator sets various parameters required for analysis or registers the reagent and the sample through the operation screen of the display device 103. In addition, after the measurement, the operator checks the analysis result through the operation screen on the display device 103.

In addition, analysis of a blood coagulation time item by the automatic analyzer 1 is performed according to the following procedure.

First, an operator requests an examination item for each sample using the input device 107 such as a keyboard. In order to analyze the sample for the requested examination item, the reaction container transport mechanism 23 transports the disposable reaction container (for blood coagulation analysis) 28 from the reaction container magazine 25 to the sample dispensing position 18. The sample dispensing mechanism 12 dispenses a predetermined amount of the sample from the sample container 27 into the reaction container (for blood coagulation analysis) 28 according to analysis parameters.

The reaction container (for blood coagulation analysis) into which the sample is dispensed is transported to the reaction port 301 of the blood coagulation time detecting part by the reaction container transport mechanism 23 and is heated to a predetermined temperature. The first reagent dispensing mechanism 17 dispenses a predetermined amount of reagent solution into the reaction container (for biochemical analysis) 26 on the reaction disk 13 according to analysis parameters of the corresponding examination item. In the reaction disk 13, a thermostat (not illustrated) is provided. Therefore, the reagent solution dispensed into the reaction container (biochemical analysis) 26 is heated to 37° C.

Next, the blood coagulation reagent dispensing mechanism 30 suctions the reagent dispensed into the reaction container (for biochemical analysis) 26, the reagent is heated to a predetermined temperature by the heating part 32 in the blood coagulation reagent dispensing mechanism 30, and the heated reagent is discharged into the reaction container (for blood coagulation analysis) 28.

When the reagent is discharged, photometry of transmitted light or scattered light of light emitted to the reaction container (for blood coagulation analysis) 28 starts. The transmitted light or the scattered light having undergone photometry is converted into numeric data in proportion to the light amount by the A/D converter (2) 203, and the numeric data is input to the computer 105 through the interface 101.

The time required for blood coagulation reaction (hereinafter, also simply referred to as "blood coagulation time) is obtained using the converted numerical value. For example, regarding an examination item such as APTT (activated partial thromboplastin time), the blood coagulation time obtained as described above is output as the analysis result. Here, regarding an examination item such as Fbg (fibrinogen), component concentration data is further obtained with respect to the obtained blood coagulation time and is output as the analysis result on the basis of a calibration curve measured in advance using the converted numerical value with an analysis method designated per examination item. The blood coagulation time or the component concentration data as the analysis result of each examination item is output to the printer 106 or the screen of the display device 103.

Here, before performing the above-described measuring operation, the operator sets various parameters required for analysis or registers the reagent and the sample in advance through the operation screen of the display device 103. In addition, after the measurement, the operator can check the analysis result through the operation screen on the display device 103.

In addition, the place into which the sample is discharged by the sample dispensing mechanism 12 may be the reaction container (for biochemical analysis) 26. In this case, after causing the sample to react with the pre-treatment solution in advance in the reaction container (for biochemical analysis) 26, the sample can be dispensed into the reaction container (for blood coagulation analysis) 28 by the blood coagulation reagent dispensing mechanism 30.

In the blood coagulation reagent dispensing mechanism 30, stirring called discharge stirring is performed, the discharge stirring being a method of mixing the reagent with the sample in the reaction container (for blood coagulation analysis) 28 using a force with which the reagent is discharged to the sample stored in the reaction container (for blood coagulation analysis) 28 in advance. Regarding the dispensing order of the sample and the reagent, the reagent may be dispensed before the sample contrary to the example. In this case, the sample can be mixed with the reagent using a force with which the sample is discharged.

Here, in the discharge stirring, in order to reliably perform stirring, it is important to secure high accuracy of the position of a tip position of the blood coagulation reagent dispensing mechanism 30 relative to the reaction container, and particular attention is required for the position adjustment.

<Analysis Operation of Blood Coagulation Reagent Dispensing Mechanism>

A sequence of the analysis operation of the blood coagulation reagent dispensing mechanism 30 according to the embodiment will be described using FIGS. 3 and 4. The sequence of the analysis operation mainly includes an analysis preparation sequence, a reagent dispensing sequence, and a nozzle cleaning sequence.

FIG. 3 is a diagram illustrating a series of operations of the blood coagulation reagent dispensing mechanism to which an operation of supplying heated system water according to the embodiment is not applied. Here, "cell" in this drawing and FIGS. 4 and 5 corresponds to "reaction container (for biochemical analysis) 26" in the following description. When an empty time is present at the start of analysis or during a requested analysis, the blood coagulation reagent dispensing mechanism 30 stands by in the cleaning tank 40 for a blood coagulation reagent dispensing mechanism (FIG. 3 (1)). At this time, the nozzle part 35 is exposed from the heating part and thus is exposed to external air such that the temperature of the nozzle part 35 is generally lower than that of the heating part 32. For example, in an environment in which the external air temperature is 25° C., the heating part 32 is 39° C., whereas the base temperature and the tip temperature of the nozzle part 35 are about 38° C. and about 26° C., respectively.

Next, as the reagent dispensing sequence, the blood coagulation reagent dispensing mechanism 30 moves to the reaction container (for biochemical analysis) 26, suctions segmented air, and suctions the reagent (37° C.) dispensed into the reaction container (for biochemical analysis) 26 (FIG. 3 (2)). Next, in order to heat the suctioned reagent, air is suctioned to draw the reagent in the nozzle part 35 into the heating block 31 (FIG. 3 (3)). Next, the blood coagulation reagent dispensing mechanism 30 moves to the blood coagulation time detecting part 21 and discharges the reagent heated to about 39° C. in the heating block 31 (of FIG. 3 (4)). During discharging, the reagent passes through the nozzle part 35. Therefore, thermal energy of the reagent is stolen by the nozzle part 35, and the temperature of the reagent decreases by about 1° C. in an environment in which the external air temperature is 25° C. and decreases by about 2° C. in an environment in which the external air temperature is 15° C. In addition, after the discharge, the reagent heated to 39° C. and the system water are temporarily stored in the nozzle part 35 such that the nozzle part 35 receives thermal energy from the liquid and is heated. After the discharging operation, the blood coagulation reagent dispensing mechanism 30 returns to the cleaning tank 40 for a blood coagulation reagent dispensing mechanism and is cleaned by the system water and the inner cleaning water (FIG. 3 (5)).

After FIG. 3 (5), as the nozzle cleaning sequence, the blood coagulation reagent dispensing mechanism 30 moves to the reaction container (for biochemical analysis) 26, suctions segmented air, and suctions a detergent (37° C.) dispensed into the reaction container (for biochemical analysis) 26 (FIG. 3 (6)). In order to clean the inside of the heating pipe 34 with the suctioned detergent, the suctioning and discharging of air is repeated (FIG. 3 (7)). After cleaning, the detergent heated to about 39° C. in the heating block 31 is discharged (FIG. 3 (8)). During discharging, the detergent passes through the nozzle part 35. Therefore, thermal energy of the detergent is stolen by the nozzle part 35, and the nozzle part 35 is heated. After discharge, the detergent is cleaned off by the system water and the inner cleaning water (FIG. 3 (9)). Next, when the analysis is not continually performed, the device returns to FIG. 3 (1) and enters the standby state. When the analysis is continually performed, the device returns to FIG. 3 (2) and starts the reagent dispensing sequence.

In the reagent dispensing sequence and the nozzle cleaning sequence, the heated liquid passes through the nozzle part 35, and the nozzle part 35 is heated in each case. Therefore, the temperature of the nozzle part 35 after the end of the analysis operation is higher than that of the nozzle part 35 in the standby state by about 2° C. Accordingly, after the standby state, there is a difference between the temperature of the reagent discharged at the start of analysis (hereinafter, also referred to as "intermittent analysis") following the standby state and the temperature of the reagent discharged at the time of the continuous analysis. When there is a difference in the temperature of the reagent during discharge, this difference may affect the measurement result.

FIG. 4 illustrates a series of operations of the blood coagulation reagent dispensing mechanism to which the operation of supplying heated system water relating to the specimen according to the embodiment is applied in order to the effect of the temperature difference described above with reference to FIG. 3. Here, before the sequence proceeds from the analysis preparation sequence to the reagent discharge sequence, the system water heated in the heating pipe 34 is delivered to the nozzle part 35 (FIG. 4 (1)'). The nozzle part 35 can be heated by receiving thermal energy of the heated system water. As a result, even when there is an empty time at the start of analysis or during a requested analysis and the device passes through the standby state, the difference in the temperature of the nozzle part 35 can be reduced as compared to the continuous analysis. During the continuous analysis, the device returns to FIG. 4 (2) after the cleaning operation in FIG. 4 (9) and repeats the operations described above with reference to FIG. 3. In addition, when analysis is not requested, the device returns to FIG. 4 (1) after the cleaning operation in FIG. 4 (9) and enters the standby state. When analysis starts again, the operation of FIG. 4 (1)' is performed, and then the reagent dispensing sequence and the nozzle cleaning sequence are performed. Therefore, in the automatic analyzer 1 according to the embodiment, when a liquid passes through the nozzle part 35, a decrease in the temperature of the liquid can be controlled to be constant irrespective of the analysis timing without adding a new mechanism, and the temperature of the liquid mixture can be controlled with high accuracy. As a result, high-accuracy blood coagulation analysis can be realized.

FIG. 5 is a flowchart corresponding to FIG. 4 and illustrating the series of operations of the blood coagulation reagent dispensing mechanism to which the operation of supplying heated system water according to the embodiment is applied. The operations illustrated in this drawing are performed on the basis of instructions transmitted from the computer 105 to the blood coagulation reagent dispensing control unit 204 through the interface 101.

First, analysis is requested through the input device 107. Here, at the time of the initial analysis, the temperature of the nozzle part 35 of the blood coagulation reagent dispensing mechanism 30 is low. Therefore, in Step 501, system water heated and stored in the heating pipe 34 is delivered to the nozzle part 35 (Step 501). In Step 502, the reagent for blood coagulation analysis stored in the reaction container (for biochemical analysis) 26 is suctioned (Step 502). Next, in the cleaning tank, the suctioned reagent is drawn to the heating block 31 (Step 503) and is discharged into the reaction container (for blood coagulation analysis) 28 held in the reaction port 301 of the blood coagulation time detecting part 21 (Step 504). Next, the blood coagulation reagent dispensing mechanism 30 moves to the cleaning tank and delivers the system water to the nozzle part 35 (Step 505). Next, the blood coagulation reagent dispensing mechanism 30 suctions the cleaning solution stored in the reaction container (for biochemical analysis) 26 (Step 506) and draws the suctioned cleaning solution to the heating pipe 34 to cleans the heating pipe 34 (Step 507).

Here, whether or not a dispensing operation for the next analysis is present is determined (Step 508). When the dispensing operation for the next analysis is present, since the heated reagent was dispensed just before, it is presumed that a decrease in the temperature is small. Accordingly, the device returns to Step 502 without performing Step 501 (continuous analysis). On the other hand, when the next analysis is not present, the device enters the standby state in Step 509 after cleaning (Step 509). After the standby state, whether or not the next analysis is present is determined (Step 510). When the next analysis is present, it is presumed that the temperature of the nozzle part 35 decreases during the standby. Therefore, the device returns to Step 501 (intermittent analysis). When the next analysis is not present, the analysis ends.

FIG. 6 is a time chart illustrating a series of operations of blood coagulation analysis (during the continuous analysis) according to the embodiment. FIG. 7 is a time chart illustrating a series of operations of blood coagulation analysis (during the intermittent analysis) according to the embodiment. Here, in the following description, "cell" in FIGS. 6 and 7 corresponds to "reaction container (for biochemical analysis) 26", and "measurement port" corresponds to each of the reaction ports 301 of the blood coagulation time detecting part 21. In addition, specimens No. 1 to 6, reagents No. 1 to 6, Cells No. 1 to 6, measurement ports 1 to 6, and measurements No. 1 to 6 are associated with each other. For example, in the case of the measurement No. 1, the measurement is performed after dispensing the reagent No. 1 stored in the cell 1 into the measurement port 1 into which the specimen No. 1 is dispensed. In FIGS. 6 and 7, "sample probe", "R1 reagent probe", and "coagulation reagent probe" correspond to "sample dispensing mechanism 12", "first reagent dispensing mechanism 17", and "blood coagulation reagent dispensing mechanism 30", respectively.

In the case of the continuous analysis, as illustrated in FIG. 6, the blood coagulation reagent dispensing mechanism 30 preheats the nozzle part 35 only at a timing before dispensing the reagent No. 1 which is the timing of the initial analysis. On the other hand, in the case of the intermittent analysis, as illustrated in FIG. 7, the standby time is present between the dispensing of the specimen No. 3 and the dispensing of the specimen No. 4. Therefore, the blood coagulation reagent dispensing mechanism 30 preheats the nozzle part 35 not only at the timing before the dispensing of the reagent No. 1 but also at a timing before the dispensing of the reagent No. 4. The reagent No. 4 is preheated by the nozzle part 35 preheated before the dispensing of the reagent No. 4 and then is dispensed such that the measurement is performed in the measurement port 4. According to the above-described aspect, by performing a control in consideration of a decrease in the temperature of the nozzle part 35 affected by the analysis order, when a liquid passes through the nozzle part 35, the temperature of the liquid can be maintained to be constant even at any analysis timing. As a result, the temperature of the liquid mixture of the sample and the reagent can be controlled with high accuracy, and high-reliability analysis can be realized.

The present invention is not limited to the embodiment and includes various modification examples. For example, the embodiments have been described in detail in order to easily describe the present invention, and the present invention is not necessarily to include all the configurations described above. In addition, a part of the configuration of one embodiment can be replaced with the configuration of another embodiment. Further, the configuration of one embodiment can be added to the configuration of another embodiment. In addition, addition, deletion, and replacement of another configuration can be made for a part of the configuration each of the embodiments.

REFERENCE SIGNS LIST

1: automatic analyzer
2: blood coagulation time analyzing unit
11: sample disk
12: sample dispensing mechanism
13: reaction disk
14: second reagent dispensing mechanism
15: first reagent disk
16: second reagent disk
17: first reagent dispensing mechanism
18: sample dispensing position
19: photometer
21: blood coagulation time detecting part
22: optical jig magazine
23: reaction container transport mechanism
24: reaction container disposal hole
25: disposable reaction container magazine
26: reaction container (for biochemical analysis) (first reaction container)
27: sample container
28: reaction container (for blood coagulation analysis) (second reaction container)
30: blood coagulation reagent dispensing mechanism
31: heating block
32: heating part
33: temperature measuring part
34: heating pipe
35: nozzle part
40: cleaning tank for blood coagulation reagent dispensing mechanism
101: interface
102: external output medium
103: display device
104: memory
105: computer
106: printer
107: input device
201: sample dispensing control unit
202: transport mechanism control unit
203: A/D converter (2)
204: blood coagulation reagent dispensing control unit
205: A/D converter (1)
206: reagent dispensing control unit (1)
207: reagent dispensing control unit (2)
301: reaction port

The invention claimed is:

1. An automatic analyzer comprising:
a reagent dispensing mechanism having a nozzle part configured to dispense a reagent;
a cleaning water supply configured to supply a cleaning water to the reagent dispensing mechanism, the cleaning water supply part including a water supply tank and a liquid delivery pump, the water supply tank storing cleaning water and the liquid delivery pump delivering the cleaning water stored in the water supply tank;
a heater configured to increase a temperature of the cleaning water to be supplied from the cleaning water supply to the reagent dispensing mechanism to a predetermined temperature;
a control unit configured to control the reagent dispensing mechanism, the heater, and the cleaning water supply, the control unit including an input part configured to receive analysis request information and a memory configured to store the analysis request information; and
a biochemical analyzing part including a first light source and a first detecting part, the first light source emitting light to a liquid mixture of the sample and the reagent that is stored in the first reaction container arranged in the reaction disk, and the first detecting part detecting the emitted light, wherein
the control unit is configured to determine whether dispensing operation for next analysis is continually performed or intermittent based on the analysis request information stored in the memory and control operation of the reagent dispensing mechanism and the cleaning water supply such that, if the dispensing operation for the next analysis is intermittent, in a cycle before a cycle in which the dispensing operation is started, the cleaning water stored in the water supply tank is delivered by the liquid delivery pump, the temperature of the delivered cleaning water is increased by the heater, and the cleaning water of the increased temperature is then supplied to the nozzle part of the reagent dispensing mechanism, and
if the dispensing operation for the next analysis is continually performed, the control unit controls the operation of cleaning water supply part such that the cleaning water stored in the water supply tank is delivered by the liquid delivery pump, and the delivered cleaning water is supplied to the nozzle part of the reagent dispensing mechanism without increasing the temperature of the cleaning water.

2. The automatic analyzer according to claim 1, wherein
if the dispensing operation for the next analysis is intermittent, the control unit controls the operation of the reagent dispensing mechanism such that the reagent dispensing mechanism starts to dispense the reagent after discharging the cleaning water supplied to the nozzle part and of the increased temperature.

3. The automatic analyzer according to claim 1, wherein the temperature increasing part is arranged between the cleaning water supply part and the nozzle part of the reagent dispensing mechanism.

4. The automatic analyzer according to claim 1, wherein the heater includes a heating block.

5. An automatic analyzer comprising:

a rotatable reaction disk in which a first reaction container for mixing a sample and a reagent with each other for a reaction is circumferentially arranged;

a reaction port in which a second reaction container for mixing a sample and a reagent with each other for a reaction is arranged;

a first reagent dispensing mechanism configured to dispense the reagent into the first reaction container;

a second reagent dispensing mechanism having a nozzle part for dispensing the reagent into the second reaction container;

a cleaning water supply part including a water supply tank and a liquid delivery pump, the water supply tank storing a cleaning water and the liquid delivery pump supplying the cleaning water stored in the water supply tank to the second reagent dispensing mechanism;

a heater configured to increase a temperature of cleaning water to be supplied from the cleaning water supply part to the second reagent dispensing mechanism to a predetermined temperature; and a control unit configured to control the first reagent dispensing mechanism, the second reagent dispensing mechanism, the heater, and the cleaning water supply part, the control unit including an input part configured to receive analysis request information and a memory configured to store the analysis request information; and a biochemical analyzing part including a first light source and a first detecting part, the first light source emitting light to a liquid mixture of the sample and the reagent that is stored in the first reaction container arranged in the reaction disk, and the first detecting part detecting the emitted light, wherein the control unit is configured to determine whether dispensing operation for next analysis is continually performed or intermittent based on the analysis request information stored in the memory and control operation of the second reagent dispensing mechanism and the cleaning water supply part such that, if the dispensing operation for the next analysis is intermittent, in a cycle before a cycle in which the dispensing operation is started, the cleaning water stored in the water supply tank is delivered by the liquid delivery pump, the temperature of the delivered cleaning water is increased by the heater, and the cleaning water of the increased temperature is then supplied to the nozzle part of the second reagent dispensing mechanism, and if the dispensing operation for the next analysis is continually performed, the control unit controls the operation of cleaning water supply part such that the cleaning water stored in the water supply tank is delivered by the liquid delivery pump, and the delivered cleaning water is supplied to the nozzle part of the second reagent dispensing mechanism without increasing the temperature of the cleaning water.

6. The automatic analyzer according to claim 5, wherein the heater is arranged between the cleaning water supply part and the nozzle part of the second reagent dispensing mechanism.

7. The automatic analyzer according to claim 5, wherein the heater includes a heating block.

8. The automatic analyzer according to claim 5, further comprising:

a blood coagulation analyzing part including a second light source and a second detecting part, the second light source emitting light to a liquid mixture of the sample and the reagent that is stored in the second reaction container arranged in the reaction port, and the second detecting part detecting the emitted light, wherein if the dispensing operation for the next analysis is intermittent, the control unit controls the operation of the second reagent dispensing mechanism such that the second reagent dispensing mechanism starts to dispense the reagent after discharging the cleaning water supplied to the nozzle part and of the increased temperature.

9. An analysis method of an automatic analyzer the automatic analyzer including a reagent dispensing mechanism having a nozzle part for dispensing a reagent, a cleaning water supply configured to supply a cleaning water to the reagent dispensing mechanism, the cleaning water supply including a water supply tank and a liquid delivery pump, the water supply tank storing cleaning water and the liquid delivery pump delivering the cleaning water stored in the water supply tank, a heater configured to increase a temperature of the cleaning water to be supplied from the cleaning water supply to the reagent dispensing mechanism to a predetermined temperature, a control unit configured to control the reagent dispensing mechanism, the heater, and the cleaning water supply, the control unit including an input part configured to receive analysis request information and a memory configured to store the analysis request information, and a biochemical analyzing part including a first light source and a first detecting part, the first light source emitting light to a liquid mixture of the sample and the reagent that is stored in the first reaction container arranged in the reaction disk, and the first detecting part detecting the emitted light, wherein the control unit is configured to determine whether dispensing operation for next analysis is continually performed or intermittent based on the analysis request information stored in the memory and controls operation of the reagent dispensing mechanism and the cleaning water supply such that, if the dispensing operation for the next analysis is intermittent, in a cycle before a cycle in which the dispensing operation is started, the cleaning water stored in the water supply tank is delivered by the liquid delivery pump, the temperature of the delivered cleaning water is increased by the heater, and the cleaning water of the increased temperature is then supplied to the nozzle part of the reagent dispensing mechanism, and if the dispensing operation for the next analysis is continually performed, the control unit controls the operation of cleaning water supply part such that the cleaning water stored in the water supply tank is delivered by the liquid delivery pump, and the delivered cleaning water is supplied to the nozzle part of the second reagent dispensing mechanism without increasing the temperature of the cleaning water.

* * * * *